United States Patent [19]

Paszner et al.

[11] 4,409,032

[45] Oct. 11, 1983

[54] ORGANOSOLV DELIGNIFICATION AND SACCHARIFICATION PROCESS FOR LIGNOCELLULOSIC PLANT MATERIALS

[75] Inventors: Laszlo Paszner, Vancouver; Pei-Ching Chang, Burnaby, both of Canada

[73] Assignee: Thermoform Bau-Und Forschungsgesellschaft, Murten, Switzerland

[21] Appl. No.: 248,023

[22] Filed: Mar. 26, 1981

Related U.S. Application Data

[63] Continuation-in-part of Ser. No. 135,175, Mar. 28, 1980, abandoned, which is a continuation of Ser. No. 28,447, Apr. 9, 1979, abandoned, which is a continuation of Ser. No. 932,421, Aug. 11, 1978, abandoned.

[30] Foreign Application Priority Data

Aug. 31, 1977 [CA] Canada ................................ 285821

[51] Int. Cl.$^3$ .............................................. C13K 1/02
[52] U.S. Cl. ........................................ 127/37; 162/72; 162/14; 162/76
[58] Field of Search .................. 162/76, 77, 80, 82, 162/81, 72, 16, 14; 127/37, 43

[56] References Cited

U.S. PATENT DOCUMENTS

| 1,856,567 | 5/1932 | Kleinert et al. | 162/14 |
| 1,919,623 | 7/1933 | Dreyfus | 162/72 |
| 2,022,654 | 12/1935 | Dreyfus | 162/77 |
| 2,024,689 | 12/1935 | Groombridge | 162/76 |
| 2,042,705 | 6/1936 | Dreyfus | 162/71 |
| 2,070,585 | 2/1937 | Dreyfus | 162/77 |
| 2,703,279 | 3/1955 | Bate et al. | 162/76 |
| 2,730,444 | 1/1956 | Hodge et al. | 162/76 |
| 2,783,146 | 2/1957 | McKee | 162/76 |
| 3,479,248 | 11/1969 | Nobile | 162/16 |
| 3,585,104 | 6/1971 | Kleinert | 162/77 |
| 3,764,462 | 10/1973 | Baril | 162/16 |
| 4,100,016 | 7/1978 | Diebold et al. | 162/77 |

FOREIGN PATENT DOCUMENTS

WO79/00119 3/1979 PCT Int'l Appl. ................ 127/37

OTHER PUBLICATIONS

Chang et al., "Comparative Dissolution Rates of Carbohydrates & Lignin During Acidified Aqueous Organosolv Saccharification of Alcohol—Benzene Extracted Douglas Fir & Aspen Woods", Presented by Tapper, Forest Biology/Wood Chemisty Symposium Jun. 20–22, 1977, Madison, Wis.

Chang et al., "Recovery and GC Analysis of Wood Sugars From Organosolv Saccharification of Douglas—Fir Heartwood", Presented at the 1976 Canadian Wood Chemistry Symposium Mont Gabrial P. Q., Sep. 1–3, 1976.

Primary Examiner—William F. Smith
Attorney, Agent, or Firm—Ian C. McLeod

[57] ABSTRACT

Cellulose-containing material is rapidly saccharified to convert pentosans and hexosans to sugars by cooking under pressure at from 180° C. to 220° C. with acetone-water solvent mixture carrying from 0.05 to 0.25 weight percent of phosphoric, sulfuric or hydrochloric acids.

A predominantly cellulosic material, e.g. a delignified pulp, is hydrolysed to yield relatively pure glucose recoverable from liquor which is flowed through the cellulose, then withdrawn and cooled and neutralized within an elapsed time of a minute or less.

Whole wood is nearly totally dissolvable by the process, yielding mixed pentoses and hexoses. The dehydration and degradation products of sugars are formed by prolonging retention time of liquor from 20 to 45 minutes.

6 Claims, No Drawings

ORGANOSOLV DELIGNIFICATION AND SACCHARIFICATION PROCESS FOR LIGNOCELLULOSIC PLANT MATERIALS

CROSS REFERENCE TO RELATED APPLICATIONS

This application is a continuation-in-part of application Ser. No. 06/135,175 filed Mar. 28, 1980, which is a continuation of Ser. No. 06/028,447 filed Apr. 9, 1979 which is a continuation of Ser. No. 05/932,421 filed Aug. 11, 1978 all of which are now abandoned.

This invention relates to improved processes for saccharifying cellulosic materials, and especially to the production of sugars from lignin-hemicellulose-cellulose materials by weakly-acidified acetone-water solvent mixtures at elevated temperatures.

The invention proposes a radically accelerated saccharification process effective either to dissolve whole wood or a predominantly cellulosic residue made from wood by a pulping process capable of removing lignin and hemicelluloses. Exceptionally rapid conversion of the $\beta$-glycoside polymeric chains characterizing amorphous and crystalline cellulose is effected by treating the cellulose with an aqueous solvent mixture containing a major volume proportion of acetone and a small quantity of mineral acid, such as 0.05% to 0.25% by weight of phosphoric, sulfuric or hydrochloric.

The treatment may be effected at temperatures somewhat elevated with respect to those employed heretofore in saccharification processes, and may best be effected at between 180° C. and 225° C., and especially at temperatures between 200° C. and 220° C.

While the use of acetone in aqueous solution in a concentration of 50% to 80% containing a low concentration of mineral acid has been taught heretofore for delignification of a lignin-hemicellulose-cellulose substance such as wood chips to provide cellulosic residue, as taught in U.S. Pat. Nos. 2,022,654 and 2,106,797 to Dreyfus, no prior process has been disclosed utilizing the capability of a hot, acidified acetone-water mixture for greatly accelerating the rate of hydrolysis of cellulose to glucose, without correspondingly accelerating the rate of dehydration or degradation of glucose.

Heretofore the use of dilute acid in processes employing liquor percolation has characterized the production of wood sugars and conversion products, but these require large apparatus, long treatment times, and at best recover much less than the theoretical quantity of glucose. The unwanted conversions of pentose sugars to derivatives and of lignin to troublesome condensation compounds are drawbacks.

The present invention is based on the discovery that virtual dissolution of woods, canes, bagasse, and cereal and other crop plant stalks can be achieved with or without liquor changes, in under 30 minutes. For example, Douglas-Fir sawdust cooked at 200° C. with 60:40 acetone-water containing 0.08% by weight of HCl, with liquor circulation to pass six times the volume of the cooking vessel through the charge in 25 minutes, yielded solid residue of only 2.8% by weight of dry wood. Similarly, Aspen wood cooked with the same rate of liquid circulation yielded 3.7% by weight of residue in 25 minutes. Nearly theoretical quantities of lignin were recovered from the withdrawn liquor, with sugar products, about 2% to 3% acetic acid, 2% methanol, 3% of water-soluble lignins, and 3% of extractives, and sugar dehydration products.

Where the desired products are to be the dehydration and degradation products of sugars, namely organic acids, furfural, 2-furaldehyde, 5-hydroxymethyl-2-furaldehyde and methanol, the process requires only that the acidified solvent mixture remain in the vessel without replacement for a time at least sufficient to hydrolyze all carbohydrates, and sufficiently longer to effect dehydrations, etc., for example 30 to 40 minutes, at the higher temperatures, i.e. above 210° C.

Where the maximum yield of glucose relatively free of pentose sugars is desired, the starting material chosen should be predominantly cellulosic, i.e. a pulp residue made by any process capable of selectively delignifying the lignin-hemicellulose-cellulose starting material to a residual lignin content less than 1% of wood weight for a hardwood such as Aspen, and less than 3% for a softwood such as Douglass-Fir. Preferably, substantial amounts of pentosans should also be removed. Subsequent saccharification by acidified acetone-water at temperatures of 180° C. to 220° C. allows recovery of a liquor of which the water phase is rich in glucose, particularly when the vessel is loaded with compacted cellulosic material at a solids:liquor ratio at least 1:1 by weight, or higher.

The invention will be more clearly understood from the illustrative examples which follow.

EXAMPLE I 75 grams of pure granular cellulose as sold under the trade designation "AVICEL" was packed into an upright pressure vessel of internal volume 100 ml fitted with a supply conduit for admission of solvent mixture at its lower end and with a second conduit for withdrawal of liquor from the upper end. Screens of 200 mesh size were provided above and below the charge to retain particles. The vessel and conduits were of stainless steel. The vessel and admission conduit were placed in a heated glycerol bath maintained at 210° C.

Heated solvent mixture comprising 70 parts acetone to 30 parts water by volume, carrying 0.08% by weight of HCl was introduced continuously by pumping under pressure into the vessel, until filled, after which the mixture flow rate was maintained at a rate to limit retention time of any portion of the mixture between 15 and 30 seconds. Liquor was withdrawn from the second conduit simultaneously with the pumping in of fresh solvent mixture, at a rate such that constant vessel pressure was maintained, and the withdrawn liquor was immediately cooled and passed into an evaporator. The liquid was neutralized with lime. Acetone and other volatiles and gases were pumped off at reduced pressure, the acetone vapour being condensed and the acetone recovered and returned to the supply where fresh acid and water were added to maintain the mixture proportions indicated.

After 11 minutes while the temperature within the vessel was held at 205° C., the vessel was removed from the bath and chilled in ice water while pumping in cold fresh solvent mixture sufficient to replace warm liquor. The vessel was then opened and the residue washed in water and then with acetone and weighed after drying. The microcrystalline material weighed 2.6 grams, equivalent to 3.6% of original cellulose weight. The recovered liquors, originally 2315 ml, were evaporated to 784 ml. Sugar content was determined to be 79.2 grams, representing 98.5% of potential glucose equivalent to dissolved cellulose.

From the results above, it will be evident that by limiting the saccharification to a shorter time, as when from one-half to one-third of the original charge remains in the vessel, a substantially stronger syrup could be produced directly from the evaporator; or the acetone content may be 80-90%.

EXAMPLE II

Whole Aspen wood of particle size passing 2.5 mm by 2.5 mm screen and retained on 5.1 mm by 5.1 mm screen, having dry weight 35 grams, were charged into the vessel of Example I. The solvent mixture and the bath were heated initially to 180° C. and the pumping and withdrawal rates were adjusted for liquor retention time of 45 seconds. Withdrawn liquors were collected together during successive time intervals each of two minutes' duration, except the first interval of 3 minutes, and the vessel temperature was raised after the first three minutes to 200° C.

Lignin quantities and dissolved xylose and reducing sugars were evaluated in the respective liquors, as set out in TABLE I.

TABLE I

| SACCHARIFICATION OF ASPEN; Acetone-Water 0.08% HCl | | | | |
|---|---|---|---|---|
| TEMPERATURE °C. | TIME INTERVAL MINUTES | LIGNIN RECOVERED % OF WOOD | XYLOSE % OF WOOD WT. | REDUCING SUGARS % OF WOOD |
| 180 | 3 | 13.37 | 14.9 | 3.8 |
| 200 | 2 | 4.03 | 1.0 | 13.3 |
| 200 | 2 | 0.4 | — | 12.1 |
| 200 | 2 | — | — | 8.3 |
| 200 | 2 | — | — | 7.9 |
| 200 | 2 | — | — | 5.2 |
| TOTALS | | 17.8 | 15.9 | 50.6 |

EXAMPLE III

Whole Douglass-Fir wood of particle sizes as in Example II was treated as described for Aspen wood, and the materials recovered from the withdrawn liquor collected in similar collection intervals. The recovered lignin and sugars are shown in Table II.

TABLE II

| SACCHARIFICATION OF DOUGLAS-FIR, Acetone-water, 0.10% HCL | | | | |
|---|---|---|---|---|
| TEMPERATURE °C. | TIME INTERVAL, MINUTES | LIGNIN RECOVERED, % OF WOOD | MANNOSE % OF WOOD WT. | REDUCING SUGARS, % OF WOOD |
| 180 | 3 | 12.4 | 10.3 | 9.9 |
| 200 | 2 | 8.1 | 1.0 | 17.1 |
| 200 | 2 | 3.8 | — | 9.0 |
| 200 | 2 | 1.8 | — | 6.2 |
| 200 | 2 | 0.5 | — | 5.2 |
| 200 | 2 | — | — | 5.0 |
| TOTALS | | 26.6 | 11.3 | 52.4 |

As evident in Tables II and III, the wood lignin is virtually completely removed within about 7 minutes from commencement of cooking. After evaporation of acetone from the collected withdrawn liquors, lignin in finely particulate form is recovered by filtration from the syrup, and is readily washed free of sugar to produce a free-flowing powder. The powder is readily soluble in conventional lignin solvents, and comprises lower molecular weight polymers ranging from MW 392-2800.

Because acetone-water and a strong mineral acid, such as sulfuric, phosphoric, or hydrochloric, vigorously hydrolyses wood carbohydrates, it will be seen that substantial amounts of glucose and other hexoses are formed during the initial intervals when the bulk of pentoses such as xylose and mannose are formed. For purposes of fermentation it may be preferable that such mixing be avoided, by first preparing a mainly cellulosic pulp using other processes effective by delignify and hydrolyse pentoses predominantly, leaving $\beta$-glucoside residue unattacked for later saccharification. Accordingly, we prefer a process of selective delignification removing lignin and a large part of hemicelluloses by use of an alcohol-water solvent mixture employing one of the organic acid catalysts, salicylic, O-phthalic, oxalic, and succinic, where the intended saccharification product is glucose for fermentation or food.

The following Example illustrates the advantageously high yield of pulp at low lignin content comprising mainly cellulose by cooking at elevated temperature for times up to one hour.

EXAMPLE IV

Spruce wood chips were cooked in a stainless steel batch type digester under pressure employing alcohol-water solvent mixtures of 70:30 and 60:40 proportions, at temperatures between 200° C. and 220° C., using minor quantities of an organic acid selected from the group oxalic, succinic, salicylic and O-phthalic, between 0.5% by weight of solvent mixture and 1%.

The cellulosic residues from the respective cooks were washed with acetone and then with water, and dried to determine yield expressed as percentage of dry wood weight. The fibers were analysed by standard TAPPI methods to determine residual lignin and viscosity, as shown in Table III.

TABLE III

| SPRUCE WOOD PULPING, ALCOHOL-WATER AND SELECTED ORGANIC ACIDS. WOOD:LIQUOR RATIO 1:10 | | | | | |
|---|---|---|---|---|---|
| MIXTURE and ACID % | | TEMPERATURE °C. | TIME MIN. | YIELD, Wt. % | TAPPI VISC. 0.5 g | LIGNIN KAPPA No. |
| Methanol | 70 | | 30 | 54.7 | 24 | 52 |
| Water | 30 | 220 | | | | |
| Salicylic | 0.7 | | 40 | 50.8 | 21 | 32 |
| Methanol | 60 | | 20 | 53 | 22 | 65 |
| Water | 40 | 200 | | | | |
| Oxalic | 0.5 | | 30 | 51 | 19 | 49 |
| Ethanol | 60 | | | | | |
| Water | 40 | 200 | 20 | 60 | 15 | 95 |
| o-Phthalic | 0.9 | | | | | |
| Ethanol | 60 | | 10 | 67 | 14 | 120 |
| Water | 40 | 200 | 20 | 57 | 11 | 79 |
| Oxalic | 0.5 | | 25 | 52 | 10 | 35 |
| Ethanol | 60 | | | | | |
| Water | 40 | 200 | 60 | 54 | 9.5 | 81 |
| Succinic | 0.6 | | | | | |

By extending the cooking time appropriately, a mainly cellulosic residue low in lignin and hemicelluloses can be obtained. Any suitable apparatus may be utilized as known in the art, for batch or continuous feeding, with or without liquor circulation and admission of fresh solvent mixture. Those skilled in the art will be aware of the necessity of effecting a separation of lignin from recovered liquor to avoid condensation on the fibres where liquor recirculation is carried out. The pulp is preferably washed with acetone.

An important advantage of the foregoing process for producing a predominantly cellulosic material from a lignin-hemicellulose-cellulose starting material, is that the dissolved lignin recoverable from the cooking liquor is not degraded or contaminated by organic substituents, so that its solubility, chemical properties and utilizability remain excellent. A relatively pure form of lignin is therefore obtained inherently as a valuable byproduct, which has properties close to those of native lignin.

It is to be understood that in addition to hydrochloric acid, there may advantageously be used either phosphoric acid or sulfuric acid, suitable concentrations of these acids being in the range 0.15% by weight of mixture to 0.25%. Very effective concentrations have been found to be 0.2% where a difficult-to-delignify starting material such as Douglass-Fir is treated. These acids require somewhat longer cooking times to hydrolyze β-glucoside, phosphoric acid-containing saccharifying mixtures requiring the longest times, e.g. above 40 minutes at 200° C. for dissolution of micro-crystalline cellulose. A higher cooking temperature, such as 210° C. to 225° C. may be resorted to. Care however should be taken to minimize the length of time sugar is exposed to the solvent mixture at such elevated temperatures. Nevertheless, the ease of separating insoluble compounds such as barium sulfate and calcium phosphate from syrups following acid neutralization is of advantage where salt-free glucose is desired.

We claim:

1. In a process for the production of carbohydrate hydrolysates of cellulose from a cellulosic material which can contain lignin by treating the material in a pressure vessel with a solvent mixture with water containing a small quantity of a mineral acid selected from the group consisting of hydrochloric, sulfuric and phosphoric acids at an elevated temperature to solubilize the carbohydrate and until sugars are formed by hydrolysis from the solubilized carbohydrate in a liquor the improvement which comprises the steps of:
   (a) supplying a solvent mixture containing acetone and water in a volume ratio of acetone to water between 70 to 30 and 60 to 40 and the acid in an amount of between 0.05 and 0.25 percent by weight of the mixture of hydrochloric acid or between 0.15 and 0.25 percent by weight of the mixture of phosphoric or sulfuric acids into the vessel under pressure with the cellulosic material to provide a limited retention time of the solvent mixture in the vessel of seven minutes or less such that sugars are not dehydrated or degraded into non sugars and then removing the solvent mixture as the liquor containing the sugars wherein the liquor removed from the vessel initially contains lignin and is separated from the liquor collected subsequently which contains the sugars;
   (b) rapidly cooling the liquor immediately upon removal from the vessel to prevent degradation of the sugars to non sugars;
   (c) recovering the sugars from the cooled liquor.

2. The process of claim 1 wherein the cellulosic material is a pulp.

3. The process of claim 1 wherein the liquor is continuously removed and cooled and fresh solvent mixture is supplied into the vessel so that sugars are exposed to heat for seven minutes or less.

4. The process of claim 1 wherein the withdrawn liquor is evaporated to separate acetone as a vapour from the aqueous liquor, and the vapour is condensed and recycled.

5. The process of claim 1 wherein the process is stopped at the time when a microcrystalline residue remains.

6. In a process for the production of carbohydrate hydrolysates and lignins from a lignocellulosic material, by treating the material in a pressure vessel with a solvent mixture with water containing a small quantity of an acid selected from the group consisting of hydrochloric, sulphuric and phosphoric acids at an elevated temperature to solubilize the carbohydrate and lignins and until sugars are formed in solubilized form in a liquor the improvement which comprises the steps of:
   (a) supplying a solvent mixture containing the acid in an amount between 0.05 and 0.25 percent by weight of the mixture of hydrochloric acid or between 0.15 and 0.25 percent by weight of the mixture of sulfuric or phosphoric acids, water and acetone in a volume ratio of acetone to water of between 70 to 30 and 60 to 40 into the vessel under pressure to provide a limited retention time of the solvent mixture in the vessel of seven minutes or less and then removing the solvent mixture as the liquor, wherein the liquor collected initially from the vessel contains the lignin and is separated from liquor collected subsequently after the liquor with the lignin is removed which contains the sugars, and wherein the sugars from the hydrolysis are not dehydrated or degraded into non-sugars;
   (b) rapidly cooling the hydrolysis liquors as they are removed from the vessel to prevent degradation of sugars to non sugars by removing the acetone wherein the lignins in the liquor collected initially are precipitated by the removal of the acetone;
   (c) removing the precipitated lignin from the hydrolysis liquor collected initially; and
   (d) recovering the sugars from the hydrolysis liquors collected initially and subsequently.

* * * * *

UNITED STATES PATENT AND TRADEMARK OFFICE
CERTIFICATE OF CORRECTION

PATENT NO. : 4,409,032
DATED : October 11, 1983
INVENTOR(S) : Laszlo Paszner

It is certified that error appears in the above-identified patent and that said Letters Patent are hereby corrected as shown below:

```
First page, under the heading "OTHER PUBLICATIONS",
     line 5, "Tapper" should be --Tappi-- and "Chemisty"
     should be --Chemistry--;
     line 10 "Gabrial" should be --Gabriel--.
```

Column 2, line 19, "Douglass" should be --Douglas--.

Column 2, line 53, "liquid" should be --liquor--.

Column 3, line 13, "were" should be --was--.

Column 3, line 41, "Douglass" should be --Douglas--.

Column 4, line 12, "by" should be --to--.

Column 5, line 20, "Douglass" should be --Douglas--.

Signed and Sealed this

Twelfth Day of June 1984

[SEAL]

Attest:

GERALD J. MOSSINGHOFF

Attesting Officer

Commissioner of Patents and Trademarks